(12) United States Patent
Sakai et al.

(10) Patent No.: US 8,385,623 B2
(45) Date of Patent: Feb. 26, 2013

(54) RADIOGRAPHIC APPARATUS

(75) Inventors: Takihito Sakai, Kyoto (JP); Masahiro Tanaka, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 656 days.

(21) Appl. No.: 12/667,523

(22) PCT Filed: Jul. 11, 2007

(86) PCT No.: PCT/JP2007/063827
§ 371 (c)(1),
(2), (4) Date: Dec. 31, 2009

(87) PCT Pub. No.: WO2009/008070
PCT Pub. Date: Jan. 15, 2009

(65) Prior Publication Data
US 2010/0183215 A1 Jul. 22, 2010

(51) Int. Cl.
*G06K 9/00* (2006.01)
(52) U.S. Cl. .......................................... 382/132; 378/62
(58) Field of Classification Search .......... 382/128–134; 378/205, 207, 62, 98.12
See application file for complete search history.

(56) References Cited

U.S. PATENT DOCUMENTS

2007/0041508 A1* 2/2007 Tubbs ............................ 378/207
2010/0074505 A1* 3/2010 Oogami ........................ 382/132

FOREIGN PATENT DOCUMENTS

| JP | 2003-234956 A | 8/2003 |
| JP | 2003-334186 A | 11/2003 |
| JP | 2008-122489 A | 5/2006 |

OTHER PUBLICATIONS

International Search Report for the Application No. PCT/JP2007/063827 mailed Aug. 21, 2007.
Shibata, Koichi et al., "FPD System Ni Okeru Application No Kaihatsu" ("Development of Clinical Application Techniques of FPD Digital Radiographic System"), Shimadzu Review, vol. 63, Nos. 3 & 4, pp. 144-145.

* cited by examiner

*Primary Examiner* — Hoon Song
(74) *Attorney, Agent, or Firm* — Cheng Law Group, PLLC

(57) ABSTRACT

A radiographic apparatus of this invention, imaging (slot imaging) is carried out in one operation for obtaining a plurality of radiographic images based on radiation detected with an irradiation field restricted to be narrow by the irradiation field control device. Since these plurality of radiographic images are images picked up with the irradiation field restricted to be narrow, a center calculating device can determine a shifted center of the radiographic images. A shift calculating device derives a shift of the center of the X-ray images from a positional relationship between the shifted center of the radiographic images determined and the irradiation field of a radiation detecting device. Since the shift is corrected for the plurality of radiographic images per se based on the shift determined, the shift can be corrected in one slot imaging operation. At a time of slot imaging, the shift can be corrected while determining a central point at a point of time when each image is acquired, or determining a central point all together after acquiring a series of images.

19 Claims, 11 Drawing Sheets

RADIOGRAPHIC APPARATUS

TECHNICAL FIELD

This invention relates to radiographic apparatus for carrying out radiographic imaging.

BACKGROUND ART

Conventionally, there is an apparatus that rotates and tilts a top board (receiving device) with a patient placed thereon, about the axis of a horizontal shafts, to turn the top board to a standing position, an inclined position and a horizontal position (recumbent position), and picks up images based on imaging positions (see Patent Document 1, for example). When turning the top board, as shown in Patent Document 1, an X-ray tube (radiation emitting device) and an X-ray detector (radiation detecting device) tilt as interlocked therewith, and so does a strut (support device) supporting the X-ray tube.

On the other hand, there is an apparatus that includes a collimator (irradiation field control device) disposed at an emission side of the X-ray tube for controlling an irradiation field emitted from the X-ray tube, and picks up images while moving the X-ray tube and X-ray detector parallel to the top board along a longitudinal direction of the patient in a state of the collimator operated for a restriction narrower than an irradiation field projected to the X-ray detector. Such imaging is defined in this specification as "slot imaging". There is also an apparatus that combines the above-noted technique of turning the top board and the technique of carrying out imaging with the irradiation field restricted to be narrow (i.e. slot imaging).

[Patent Document 1]
Unexamined Patent Publication No. 2003-334186 (pages 2-6, FIGS. 1, 2, 5 and 7)

DISCLOSURE OF THE INVENTION

Problem to be Solved by the Invention

However, as shown in FIG. 6, since a strut 21 supporting an X-ray tube 2 sags under its own weight when in a standing position, the X-ray tube 2, which should normally be in the position of the two-dot chain line in FIG. 6, will shift to the position of the solid line. Therefore, there is a phenomenon in which the center C of X-ray images normally obtained by imaging will shift to C' due to the weight of the strut 21 (sign 22 denotes a collimator).

The center of X-ray images may shift mechanically even if the top board is not turned. Such shifting of the center of X-ray images due to turning of the top board, or other, mechanical shifting the center of X-ray images, shifts the position of an effective image area (pixel area) of the X-ray images obtained by slot imaging. Therefore, when an effective image area including a center position is clipped without carrying out a shift correction, an area without valid data may be clipped.

This invention has been made having regard to the state of the art noted above, and its object is to provide radiographic apparatus capable of correcting a shift in time of slot imaging.

Means for Solving the Problem

To fulfill the above object, this invention provides the following construction.

A radiographic apparatus of this invention is a radiographic apparatus having a receiving device for receiving a patient thereon, a radiation emitting device for emitting radiation toward the patient, a radiation detecting device for detecting radiation transmitted through the patient, and an irradiation field control device provided for the radiation emitting device for controlling and restricting an irradiation field emitted from the radiation emitting device to be narrower than an irradiation field projected to the radiation detecting device, to carry out radiographic imaging by obtaining radiographic images based on the detected radiation, the radiographic imaging being carried out with the radiation emitting device emitting radiation and the radiation detecting device detecting the radiation while, with the irradiation field restricted to be narrow by the irradiation field control device, the radiation emitting device and the radiation detecting device move parallel to each other in the same direction along a longitudinal direction of the patient relative to the receiving device, the apparatus comprising a center calculating device for determining a shifted center of radiographic images, for a plurality of radiographic images detected in a state of the irradiation field restricted to be narrow by the irradiation field control device, and a shift calculating device for determining a shift of the center of the radiographic images from a positional relationship between the center of the radiographic images and the irradiation field of the radiation detecting device.

According to the radiographic apparatus of this invention, the irradiation field control device controls and restricts the irradiation field emitted from the radiation emitting device to be narrower than the irradiation field projected to the radiation detecting device. With the irradiation field restricted to be narrow by the irradiation field control device, radiographic imaging (i.e. slot imaging) is carried out with the radiation emitting device emitting radiation, and the radiation detecting device detecting the radiation while the radiation emitting device and radiation detecting device make parallel translation relative to the receiving device in the same direction along the longitudinal direction of the patient. Since these plurality of radiographic images are images detected and picked up with the irradiation field restricted to be narrow, the center calculating device can determine a shifted center of the radiographic images. The shift calculating device derives a shift of the center of the radiographic images from a positional relationship between the shifted center of the radiographic images determined and the irradiation field of a radiation detecting device. Since the shift is corrected for the plurality of radio-graphic images per se based on the shift determined, the shift can be corrected in one slot imaging operation. At a time of slot imaging, the shift can be corrected while determining a central point at a point of time when each image is acquired, or determining a central point all together after acquiring a series of images.

In the invention noted above, it is preferred that the center calculating device is arranged to select a predetermined number of radiographic images from the plurality of radiographic images, and determine the shifted center of the radiographic images based only on the selected radiographic images. By determining the shifted center of the radio-graphic images without using all of the plurality of radiographic images, the center calculating device can perform a high-speed arithmetic process.

In these inventions noted above, it is preferred that the center calculating device is arranged to select a predetermined pixel area narrower than an entire pixel area from the entire pixel area of the plurality of radiographic images, and determine the shifted center of the radiographic images based only on the selected pixel area. By determining the shifted center of the radiographic images without using the entire pixel area of the plurality of radiographic images, the center calculating device can perform a high-speed arithmetic process.

In these inventions noted above, the apparatus may comprise a data amount adjusting device for adjusting an amount of data used by the center calculating device based on an amount of data of the plurality of radiographic images.

In this case, when there is a large amount of data of the plurality of radiographic images, the data amount adjusting device makes an adjustment to reduce the amount of data used by the center calculating device to be small, whereby the center calculating device performs a high-speed arithmetic process. Conversely, when there is a small amount of data of the plurality of radiographic images, the data amount adjusting device makes an adjustment to increase the amount of data used by the center calculating device to be large, thereby to render the arithmetic process by the center calculating device accurate. Thus, with the data amount adjusting device adjusting the amount of data, the arithmetic process by the center calculating device can be made as desired.

In these inventions noted above, one example of data based on the plurality of radiographic images is an added image obtained by adding the plurality of radiographic images, and the center calculating device is arranged to determine the shifted center of the radiographic images based on the added image. Further, an operation is carried out for selecting a maximum pixel value of the same pixel throughout the plurality of radiographic images with respect to other same pixels, and another example of data based on the plurality of radiographic images is an image formed of pixels having the selected maximum pixel value. The center calculating device is arranged to determine the shifted center of the radiographic images based on that image. In this specification, the pixels having the selected maximum pixel value are defined as "peak hold image".

In these inventions noted above, one example in which the center calculating device determines the shifted center of the radiographic images is as follows. That is, the center calculating device is arranged, based on the plurality of radiographic images, to select a pixel having a maximum pixel value from all pixels, detect each edge based on a predetermined ratio of less than one of the selected maximum pixel value, and determine a center between the detected edges to be the shifted center of the radiographic images.

Another example in which the center calculating device determines the shifted center of the radiographic images is as follows. That is, the center calculating device is arranged, based on the plurality of radiographic images, to select a pixel having a maximum pixel value from all pixels, and determine that pixel to be the shifted center of the radiographic images.

In these inventions noted above, the radiation emitting device and the radiation detecting device may be constructed, when the receiving device is rotated and tilted about an axis of a horizontal shaft, to be tiltable with that tilting, the apparatus comprising a support device tiltable with that tilting and supporting the radiation emitting device. Particularly in the case of the apparatus which rotates and tilts the receiving device about the axis of a horizontal shaft, when the receiving device is rotated and tilted about the axis of the horizontal shaft, with this tilting the radiation emitting device and the radiation detecting device tilt, and so does the support device supporting the radiation emitting device. When the support device tilts with the above tilting, and a shift is caused by the weight of the support device due to the tilting, the shift displaces the center of radiographic images. In such a case also, at a time of slot imaging, the shift can be corrected while determining a central point at a point of time when each image is acquired, or determining a central point all together after acquiring a series of images.

In these inventions noted above, the receiving device may be controllable to a horizontal position, or the receiving device may be controllable to a standing position extending along a vertical direction.

In these inventions noted above, it is preferred that the apparatus comprises a correcting device for correcting the shift determined by the shift calculating device, for the plurality of radiographic images per se.

When the above correcting device is provided, it is preferred that the apparatus comprises a clipping device for clipping a pixel area corresponding to the irradiation field restricted to be narrow by the irradiation filed control device (i.e. an effective image area), from each of the radiographic images corrected by the correcting device. Since the above pixel area is clipped in the state of having been corrected, this can prevent a situation where an area without valid data is clipped.

When the above clipping device is provided, it is preferred that the apparatus comprises a joining device for joining, in the longitudinal direction, the pixel area clipped by the clipping device and corresponding to the irradiation field restricted to be narrow, for the respective radiographic images. A radiographic image joined in the longitudinal direction can be obtained by joining the clipped pixel areas (effective image areas) in the longitudinal direction for the respective radiographic images.

Usually, when the above clipping device is provided, a reading device is provided for reading detected radiation when correcting a shift while determining a central point at a point of time when each image is acquired, or determining a central point all together after acquiring a series of images. After radiation for an entire pixel area of the radiographic images is read by the reading device, the correcting device corrects a shift for radiographic images based on the read radiation, and the clipping device clips a pixel area (effective image area) corresponding to the irradiation field restricted to be narrow, from the entire pixel area of the corrected radiographic images.

Apart from the invention noted above, a radiographic apparatus of this invention is a radiographic apparatus having a receiving device for receiving a patient thereon, a radiation emitting device for emitting radiation toward the patient, a radiation detecting device for detecting radiation transmitted through the patient, and an irradiation field control device provided for the radiation emitting device for controlling and restricting an irradiation field emitted from the radiation emitting device to be narrower than an irradiation field projected to the radiation detecting device, to carry out radiographic imaging by obtaining radiographic images based on the detected radiation, the radiographic imaging being carried out with the radiation emitting device emitting radiation and the radiation detecting device detecting the radiation while, with the irradiation field restricted to be narrow by the irradiation field control device, the radiation emitting device and the radiation detecting device move parallel to each other in the same direction along a longitudinal direction of the patient relative to the receiving device, the radiation emitting device and the radiation detecting device being constructed, when the receiving device is rotated and tilted about an axis of a horizontal shaft, to be tiltable with that tilting, the apparatus comprising a storage device for storing a relationship between tilt angle relating to the tilting and shift of the center of the radiographic images, a read range calculating device for determining, as a read range, a pixel area corresponding to the irradiation field restricted to be narrow by the irradiation field control device, in a state of the shift corrected based on the relationship stored in the storage device, and a reading device for reading the detected radiation corresponding to the pixel area based on the read range.

According to the radiographic apparatus of this invention, the irradiation field control device controls and restricts the irradiation field emitted from the radiation emitting device to be narrower than the irradiation field projected to the radiation detecting device. With the irradiation field restricted to be narrow by the irradiation field control device, radiographic imaging (i.e. slot imaging) is carried out with the radiation emitting device emitting radiation, and the radiation detecting device detecting the radiation while the radiation emitting device and radiation detecting device make parallel translation relative to the receiving device in the same direction along the longitudinal direction of the patient. On the other hand, when the receiving device is rotated and tilted about the axis of the horizontal axis, with this tilting the radiation emitting device and radiation detecting device tilt. So, the relationship between tilt angle relating to the tilting and shift of the center of radiographic images is stored beforehand in the storage device, and in the state of a shift corrected based on the relationship stored in the storage device, a pixel area corresponding to the irradiation field restricted to be narrow by the irradiation control device (i.e. effective image area) is determined as a read range. Based on the read range, the reading device reads detected radiation corresponding to the pixel area, thereby correcting a shift caused by a tilt angle at a time of slot imaging.

In this invention noted above, it is preferred that the apparatus comprises a joining device for joining, in the longitudinal direction, a pixel area of a radiographic image based on the radiation read by the reading device, for the respective radiographic images. A radiographic image joined in the longitudinal direction can be obtained by joining the read pixel areas (effective image areas) in the longitudinal direction for the respective radiographic images.

Apart from the invention noted above, a radiographic apparatus of this invention is a radiographic apparatus having a receiving device for receiving a patient thereon, a radiation emitting device for emitting radiation toward the patient, a radiation detecting device for detecting radiation transmitted through the patient, and an irradiation field control device provided for the radiation emitting device for controlling and restricting an irradiation field emitted from the radiation emitting device to be narrower than an irradiation field projected to the radiation detecting device, to carry out radiographic imaging by obtaining radiographic images based on the detected radiation, the radiographic imaging being carried out with the radiation emitting device emitting radiation and the radiation detecting device detecting the radiation while, with the irradiation field restricted to be narrow by the irradiation field control device, the radiation emitting device and the radiation detecting device move parallel to each other in the same direction along a longitudinal direction of the patient relative to the receiving device, the radiation emitting device and the radiation detecting device being constructed, when the receiving device is rotated and tilted about an axis of a horizontal shaft, to be tiltable with that tilting, the apparatus comprising a storage device for storing a relationship between tilt angle relating to the tilting and shift of the center of the radiographic images, a reading device for reading the detected radiation, a clip range calculating device for determining, as a clip range, a pixel area corresponding to the irradiation field restricted to be narrow by the irradiation field control device, for a radiographic image based on the radiation read, in a state of the shift corrected based on the relationship stored in the storage device, and a clipping device for clipping the pixel area from an entire pixel area of the radiographic image based on the clip range.

According to the radiographic apparatus of this invention, the irradiation field control device controls and restricts the irradiation field emitted from the radiation emitting device to be narrower than the irradiation field projected to the radiation detecting device. With the irradiation field restricted to be narrow by the irradiation field control device, radiographic imaging (i.e. slot imaging) is carried out with the radiation emitting device emitting radiation, and the radiation detecting device detecting the radiation while the radiation emitting device and radiation detecting device make parallel translation relative to the receiving device in the same direction along the longitudinal direction of the patient. On the other hand, when the receiving device is rotated and tilted about the axis of the horizontal axis, with this tilting the radiation emitting device and radiation detecting device tilt. So, the relationship between tilt angle relating to the tilting and shift of the center of radiographic images is stored beforehand in the storage device, and in the state of a shift corrected based on the relationship stored in the storage device, for the radiographic image based on the radiation read, a pixel area corresponding to the irradiation field restricted to be narrow by the irradiation control device (i.e. effective image area) is determined as a clip range. Based on the clip range, the clipping device clips the pixel area (effective image area) from the entire pixel area of the radiographic image based on the clip range, thereby correcting a shift caused by a tilt angle at a time of slot imaging.

In this invention noted above, it is preferred that the apparatus comprises a joining device for joining, in the longitudinal direction, the pixel area clipped by the clipping device, for the respective radiographic images. A radiographic image joined in the longitudinal direction can be obtained by joining the clipped pixel areas (effective image areas) in the longitudinal direction for the respective radiographic images.

EFFECTS OF THE INVENTION

With a radiographic apparatus according to this invention, imaging (slot imaging) is carried out in one operation for obtaining radiographic images based on radiation detected with the irradiation field restricted to be narrow by the irradiation field control device. Since these plurality of radiographic images are images picked up with the irradiation field restricted to be narrow, the center calculating device can determine a shifted center of the radiographic images. The shift calculating device derives a shift of the center of the radiographic images from a positional relationship between the shifted center of the radiographic images determined and the irradiation field of a radiation detecting device. Since the shift is corrected for the plurality of radiographic images per se based on the shift determined, the shift can be corrected in one slot imaging operation. At a time of slot imaging, the shift can be corrected while determining a central point at a point of time when each image is acquired, or determining a central point all together after acquiring a series of images.

With a radiographic apparatus different from this invention, when imaging (slot imaging) is carried out for obtaining radiographic images based on radiation detected with the irradiation field restricted to be narrow by the irradiation field control device, the radiation emitting device and radiation detecting device tilt with rotation of the receiving device about the axis of a horizontal axis. In order to correct a shift caused by a tilt angle, a relationship between tilt angle relating to the tilting and shift of the center of radiographic images is stored beforehand in the storage device. In the state of the shift corrected, a pixel area corresponding to the irradiation field restricted to be narrow by the irradiation control device (effective image area) is determined as a read range or clip range. Based on the read range or clip range, the pixel area (effective image area) is read or clipped, thereby correcting the shift caused by the tilt angle at the time of slot imaging.

DESCRIPTION OF REFERENCES

1 . . . top board
2 . . . X-ray tube
3 . . . flat panel X-ray detector (FPD)
$9a$ . . . center calculating unit
$9b$ . . . shift calculating unit
$9c$ . . . correcting unit
$9d$ . . . data amount adjusting unit
21 . . . strut
22 . . . collimator
C . . . center of an irradiation field
C' . . . shifted center
$P_{add}$ . . . added image
$P_{PH}$ . . . peak hold image
$P_S$ . . . effective pixel area
M . . . patient

[Embodiment 1]

Figure 1:
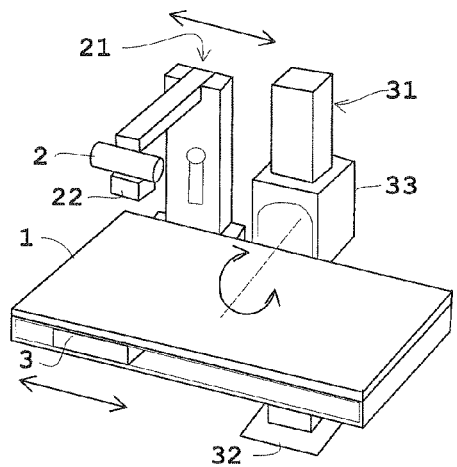
FIG. 1 is a schematic perspective view of an X-ray imaging apparatus according to each embodiment.
Figure 2:
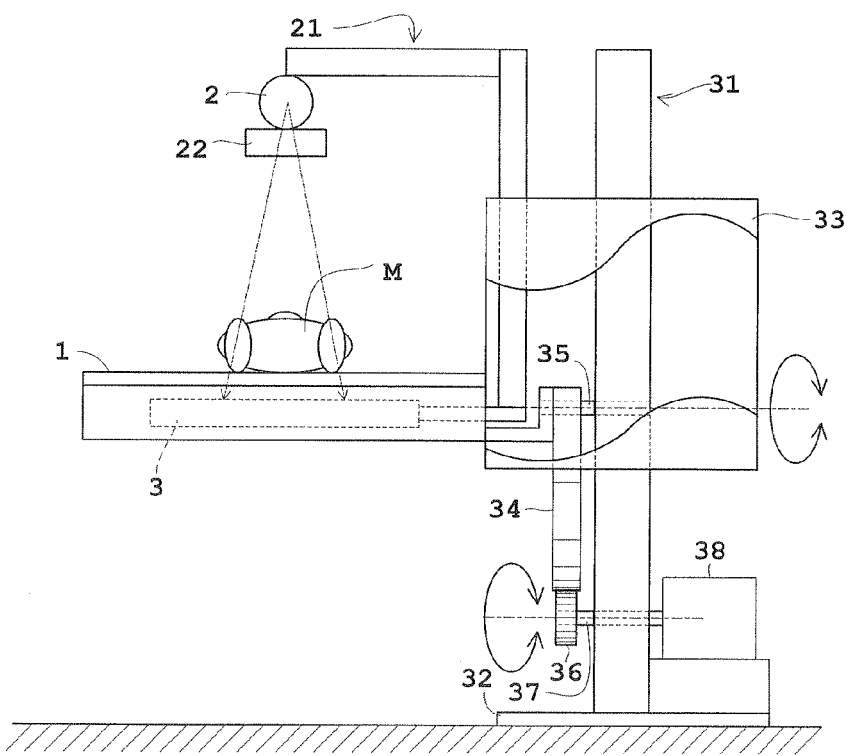
FIG. 2 is a schematic front view of the X-ray imaging apparatus according to each embodiment.
Figure 3:
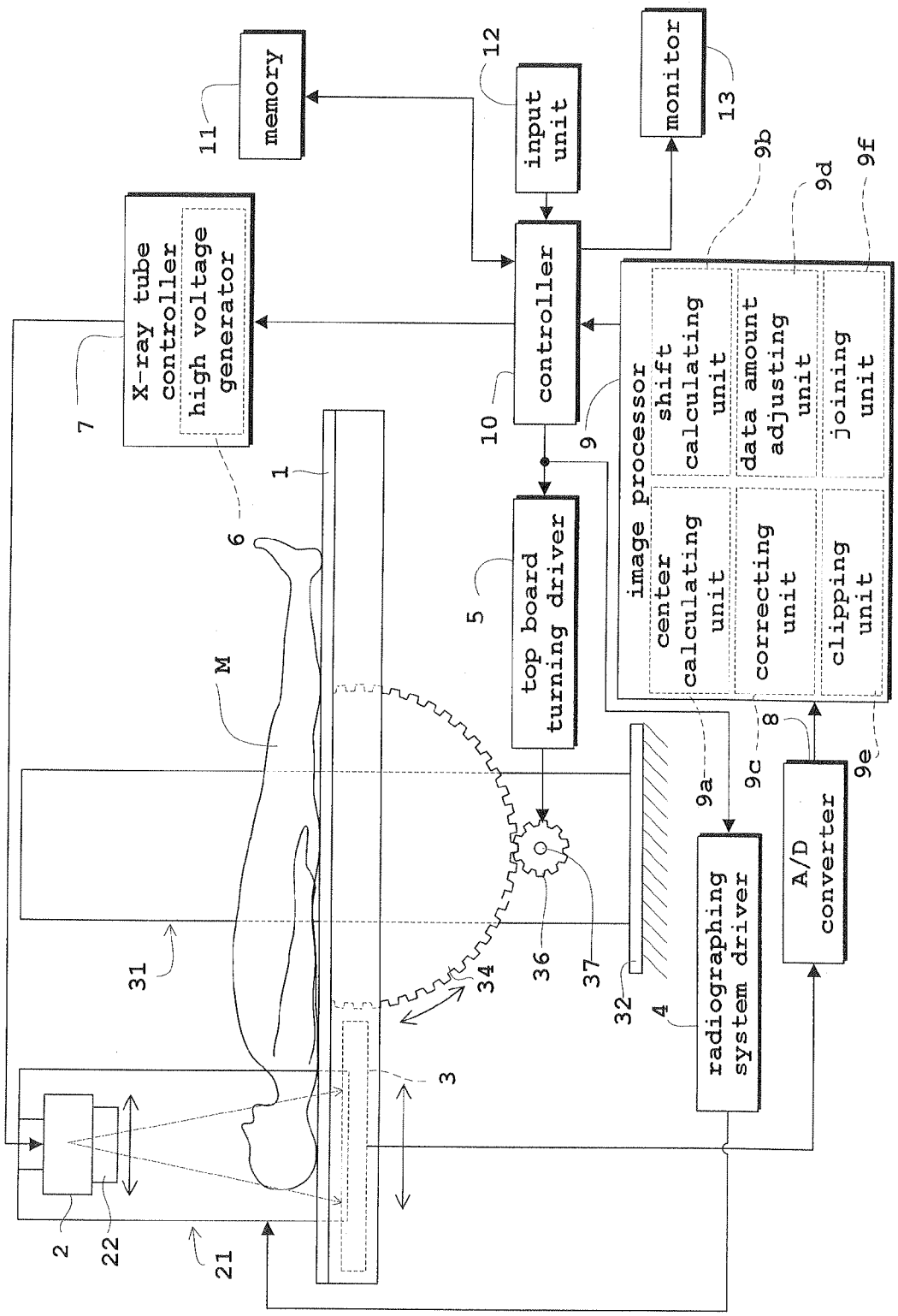
FIG. 3 is a schematic side view and block diagram of the X-ray imaging apparatus according to Embodiment 1.

Embodiment 1 of this invention will be described hereinafter with reference to the drawings. FIG. 1 is a schematic perspective view of an X-ray imaging apparatus according to Embodiment 1 including also Embodiments 2 and 3 to follow. FIG. 2 is a schematic front view of the X-ray imaging apparatus according Embodiment 1 including also Embodiments 2 and 3 to follow. FIG. 3 is a schematic side view and block diagram of the X-ray imaging apparatus according to Embodiment 1. Embodiment 1, including also Embodiments 2 and 3 to follow, will be described taking a flat panel X-ray detector (hereinafter abbreviated as "FPD") as an example of radiation detecting device, and the X-ray imaging apparatus as an example of radiographic apparatus. A top board holder and the like are not shown in FIG. 3.

As shown in FIGS. 1-3, the X-ray imaging apparatus includes a top board 1 for receiving a patient M thereon, an X-ray tube 2 for emitting X-rays toward the patient M, and an FPD 3 for detecting X-rays transmitted through the patient M. The FPD 3 is mounted in the top board 1. The top board 1 corresponds to the receiving device in this invention. The X-ray tube 2 corresponds to the radiation emitting device in this invention. The FPD 3 corresponds to the radiation detecting device in this invention.

The X-ray imaging apparatus includes a strut 21 for supporting the X-ray tube 2, and a main strut 31 for supporting the top board 1. A collimator 22 is disposed at an emission side of the X-ray tube 2 for controlling an irradiation field emitted from the X-ray tube 2. In Embodiment 1, including also Embodiments 2 and 3 to follow, with the main strut 31 supporting the X-ray tube 2 at one end thereof as noted above, and supporting, at the other end thereof, the FPD 3 mounted in the top board 1, the X-ray tube 2 and FPD 3 make parallel translation relative to the top board 1 in the same direction along the longitudinal direction of the patient M (see FIG. 3). While the X-ray tube 2 and FPD 3 make parallel translation relative to the top board 1 in the same direction along the longitudinal direction of the patient M, with the collimator 22 operated for a restriction narrower than an irradiation field projected to the FPD 3 (see FIG. 3), X-ray imaging is carried out with the X-ray tube 2 emitting X-rays, and the FPD 3 detecting the X-rays. The strut 21 corresponds to the support device in this invention. The collimator 22 corresponds to the irradiation field control device in this invention.

The main strut 31 is erected on a base 32 installed on a floor, and has a top board holder 33 for holding the top board 1 to be capable of turning (tilting) the latter. With the main strut 31 erected on the base 32 installed on the floor, and the top board holder 33 disposed for holding the top board 1, the state of the top board 1 being held provides support also for the FPD 3 mounted in the top board 1, the strut 21 supporting the FPD 3 at the other end thereof, the X-ray tube 2 supported at one end of the strut 21, and the collimator 22 disposed at the emission side of the X-ray tube 2.

The top board holder 33 has, arranged therein, a sector rack 34 for rotating and tilting the top board 1 about the axis of a horizontal shaft, a support shaft 35 extending through the sector rack 34 and main strut 31, a pinion 36 meshed with the sector rack 34, a rotary shaft 37 having the pinion 36 mounted at one end thereof, and a motor 38 for rotating the rotary shaft 37. When the motor 38 rotates the rotary shaft 37, the pinion 36 mounted at one end of the rotary shaft 37 rotates. With rotation of the pinion 36, the sector rack 34 meshed therewith rotates about the support shaft 35 using the support shaft 35 as fulcrum. The rotation of the sector rack 34 about the support shaft 35 rotates and tilts the top board 1 about the axis of the horizontal shaft.

When the top board 1 rotates and tilts about the axis of the horizontal shaft in this way, the top board 1 can be turned to a standing position, an inclined position and a horizontal position (recumbent position). With tilting of the top board 1, the X-ray tube 2 and FPD 3 tilt, and so does the strut 21 supporting the X-ray tube 2. When turning the top board 1 to the standing position, the standing position cannot be realized if the distance from a rotating position about the axis of the horizontal shaft of the top board 1 to a lower part of the top board 1 is longer than the height from the support shaft 35 of the strut 31 to a lower part of the strut 31. In this case, the standing position can be realized by moving the top board 1 upward.

As shown in FIG. 3, the X-ray imaging apparatus further includes a radiographing system driver 4 for driving a radiographing system motor (not shown) in order to cause a radiographing system including the X-ray tube 2 and FPD 3 to make parallel translation relative to the top board 1 along the longitudinal direction of the patient M, a top board turning driver 5 for driving the motor 38 (see FIG. 2) to turn (tilt) the top board 1 noted above, an X-ray tube controller 7 having a high voltage generator 6 for generating a tube voltage and tube current for the X-ray tube 2, an analog-to-digital converter 8 for digitizing and fetching X-ray detection signals which are charge signals from the FPD 3, an image processor 9 for performing various processes based on the X-ray detection signals outputted from the analog-to-digital converter 8, a controller 10 for performing an overall control of these components, a memory 11 for storing processed images, an input unit 12 for the operator to input various settings, and a monitor 13 for displaying the processed images and other information.

The high voltage generator 6 generates the tube voltage and tube current for application to the X-ray tube 2 to emit X-rays. The X-ray tube controller 7 controls, for example, setting of the irradiation field of the collimator 22. In Embodiment 1, including also Embodiments 2 and 3 to follow, the X-ray tube controller 7 controls the X-ray tube 2 to emit X-rays while the X-ray tube 2 and FPD 3 make parallel translation relative to the top board 1 in the same direction along the longitudinal direction of the patient M.

The controller 10 has a central processing unit (CPU) and other elements. The memory 11 has storage media, typically a ROM (Read-Only Memory) and RAM (Random Access Memory). The input unit 12 has a pointing device, typically a mouse, keyboard, joy stick, trackball and/or touch panel. The X-ray imaging apparatus obtains images of the patient M, with the FPD 3 detecting X-rays transmitted through the patient M, and the image processor 9 carrying out image processing based on the X-rays detected.

The image processor 9 includes a center calculating unit 9*a* for determining a shifted center of X-ray images described hereinafter, a shift calculating unit 9*b* for determining a shift, a correcting unit 9*c* for correcting the shift, a data amount adjusting unit 9*d* for adjusting an amount of data used by the center calculating unit 9*a*, a clipping unit 9*e* for clipping effective image areas corresponding to the irradiation field restricted to be narrow by the collimator 22, and a joining unit 9*f* for joining the clipped effective image areas for the respective X-ray images in a longitudinal direction. The center calculating unit 9*a* corresponds to the center calculating device in this invention. The shift calculating unit 9*b* corresponds to the shift calculating device in this invention. The correcting unit 9*c* corresponds to the correcting device in this invention. The data amount adjusting unit 9*d* corresponds to the data amount adjusting device in this invention. The clipping unit 9*e* corresponds to the clipping device in this invention. The joining unit 9*f* corresponds to the joining device in this invention. The effective image areas correspond to the pixel areas which correspond to the restricted irradiation field in this invention. Specific functions of the center calculating unit 9*a*, shift calculating unit 9*b*, correcting unit 9*c*, data amount adjusting unit 9*d*, clipping unit 9*e* and joining unit 9*f* will be described hereinafter with reference to FIGS. 6-11.

The memory 11 is constructed for writing and storing each image processed by the image processor 9. As does the controller 10, the radiographing system driver 4, top board turning driver 5 and X-ray tube controller 7 also have CPUs and so on.

Figure 4:
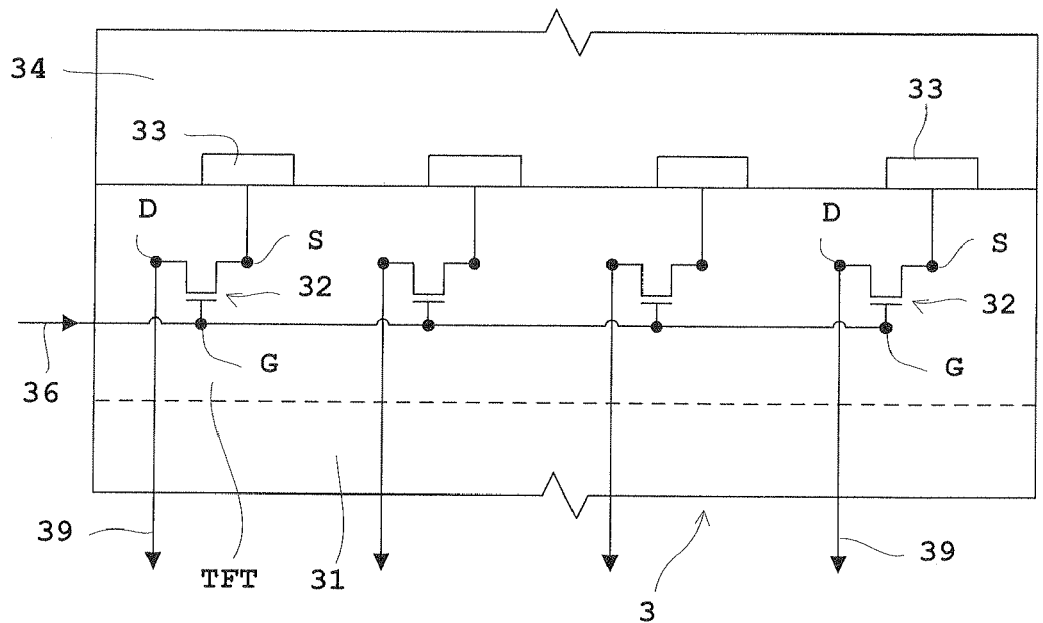
FIG. 4 is an equivalent circuit, seen in side view, of a flat panel X-ray detector (FPD)
Figure 5:
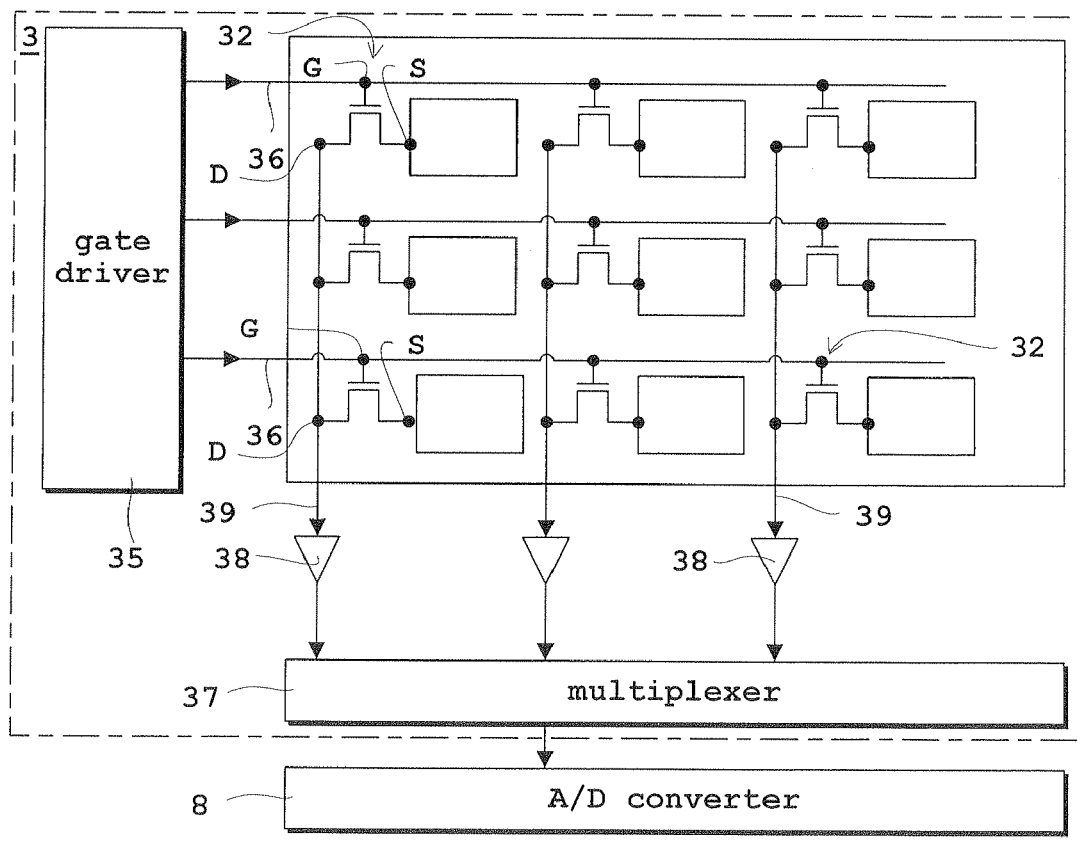
FIG. 5 is an equivalent circuit, seen in plan view, of the flat panel X-ray detector (FPD)

Next, the construction of the flat panel X-ray detector (FPD) 3 will be described with reference to FIGS. 4 and 5. FIG. 4 is an equivalent circuit, seen in side view, of the flat panel X-ray detector (FPD). FIG. 5 is an equivalent circuit, seen in plan view, of the flat panel X-ray detector (FPD).

As shown in FIG. 4, the FPD 3 includes a glass substrate 31, and thin film transistors TFT formed on the glass substrate 31. As shown in FIGS. 4 and 5, the thin film transistors TFT comprise numerous (e.g. 1,024×1,024) switching elements 32 arranged in a two-dimensional matrix of rows and columns. The switching elements 32 are formed separate from one another for respective carrier collecting electrodes 33. Thus, the FPD 3 is also a two-dimensional array radiation detector.

As shown in FIG. 4, an X-ray sensitive semiconductor 34 is laminated on the carrier collecting electrodes 33. As shown in FIGS. 4 and 5, the carrier collecting electrodes 33 are connected to the sources S of the switching elements 32. A plurality of gate bus lines 36 extend from a gate driver 35, and are connected to the gates G of the switching elements 32. On the other hand, as shown in FIG. 5, a plurality of data bus lines 39 are connected through amplifiers 38 to a multiplexer 37 for collecting charge signals and outputting as one. As shown in FIGS. 4 and 5, each data bus line 39 is connected to the drains D of the switching elements 32.

With a bias voltage applied to a common electrode not shown, the gates of the switching elements 32 are turned on by applying thereto (or reducing to 0V) the voltage of the gate bus lines 36. The carrier collecting electrodes 33 output charge signals (carriers) converted from X-rays incident on the detecting plane through the X-ray sensitive semiconductor 34, to the data bus lines 39 through the sources S and drains D of the switching elements 32. The charge signals are provisionally stored in capacitors (not shown) until the switching elements are turned on. The amplifiers 38 amplify the charge signals read out to the data bus lines 39, and the multiplexer 37 collects the charge signals, and outputs them as one charge signal. The analog-to-digital converter 8 digitizes the outputted charge signals, and outputs them as X-ray detection signals. As is clear from the above description, the amplifiers 38, data bus lines 39 and analog-to-digital converter 8 have a function to read the detected X-rays (X-ray detection signals). The amplifiers 38, data bus lines 39 and analog-to-digital converter 8 correspond to the reading device in this invention.

Figure 6:
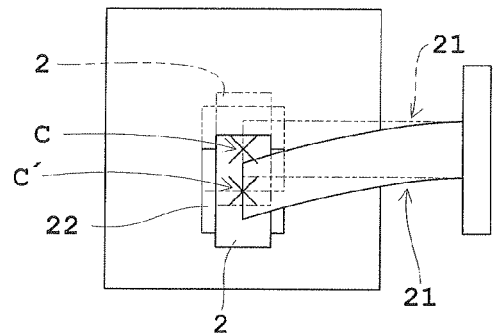
FIG. 6 is a schematic front view of an X-ray tube and a strut at a time of standing position for illustrating occurrence of a shift due to the weight of the strut.
Figure 7:
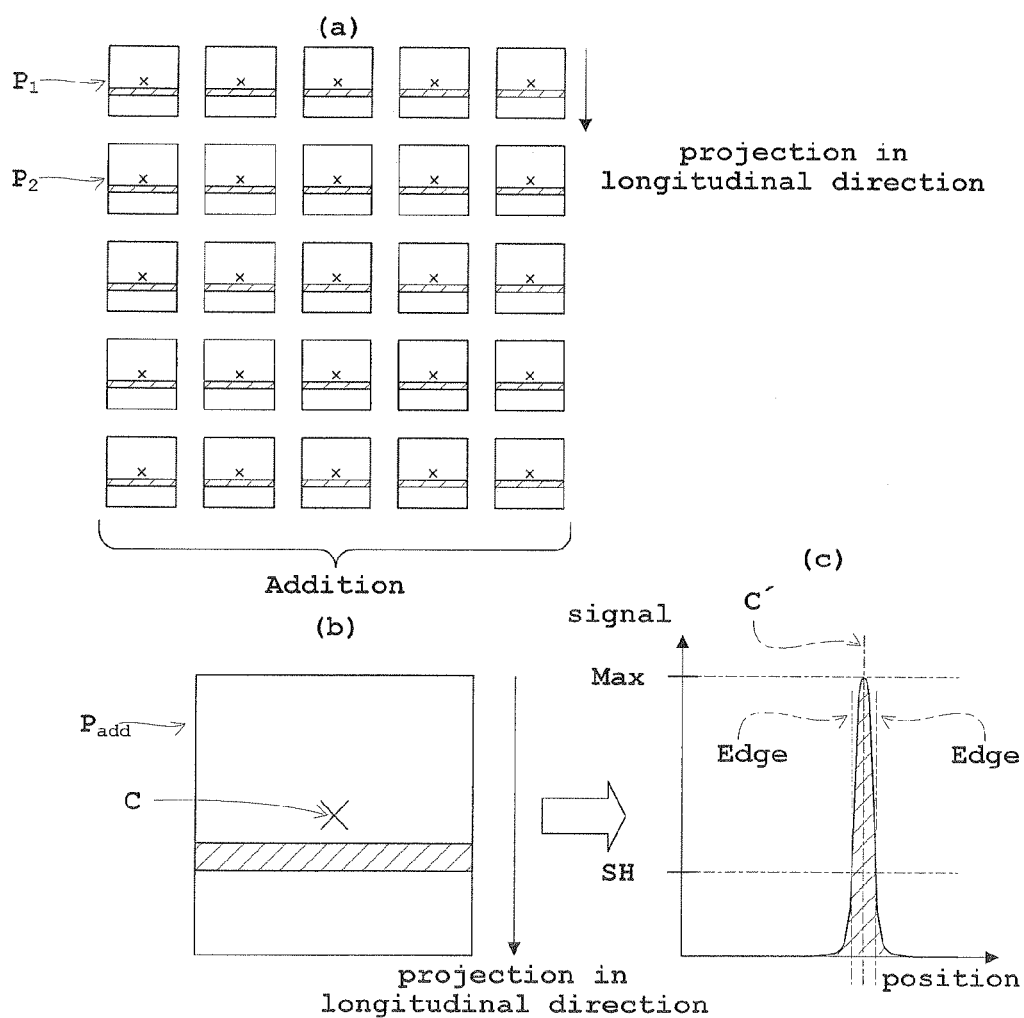
FIGS. 7 (a)-(c) are schematic views of X-ray images, an added image and a profile for illustrating an example of determining a shifted center of X-ray images.
Figure 8:
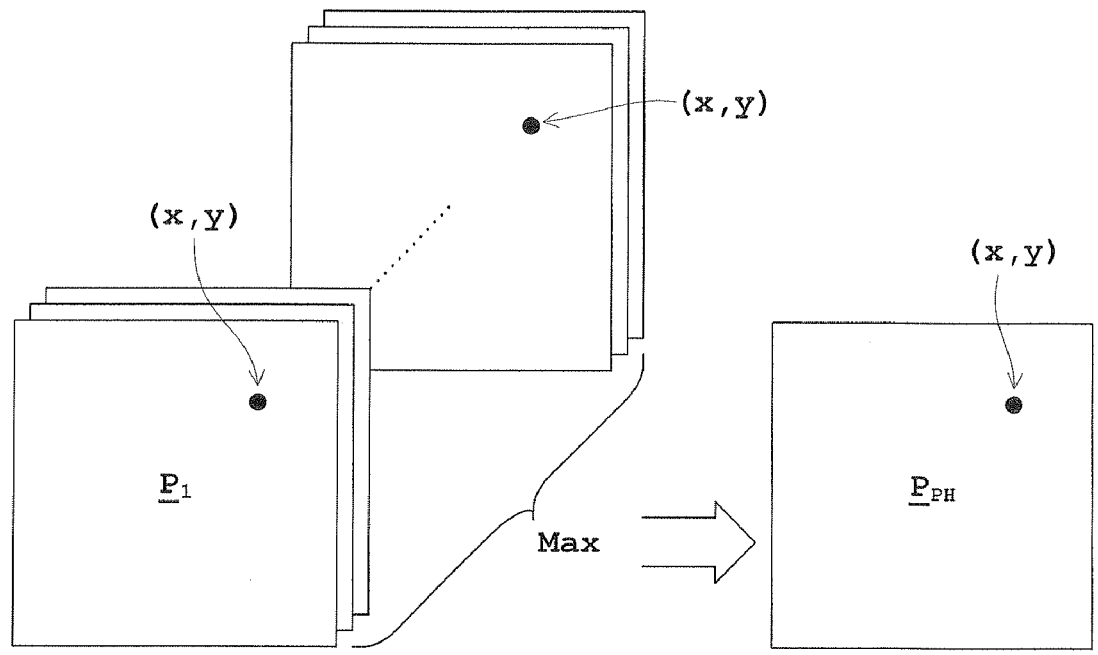
FIG. 8 is a schematic view of X-ray images and a peak hold image for illustrating another example of determining a shifted center of X-ray images.
Figure 9:
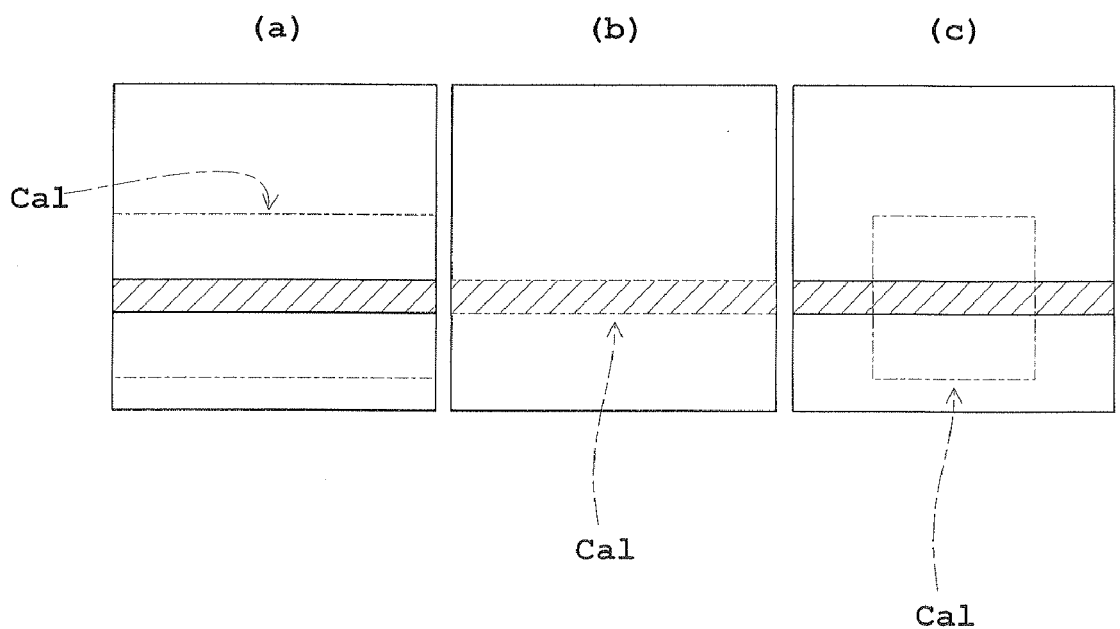
FIGS. 9 (a)-(c) are schematic views showing each example about selection of a predetermined pixel area narrower than an entire pixel area of X-ray images.
Figure 10:
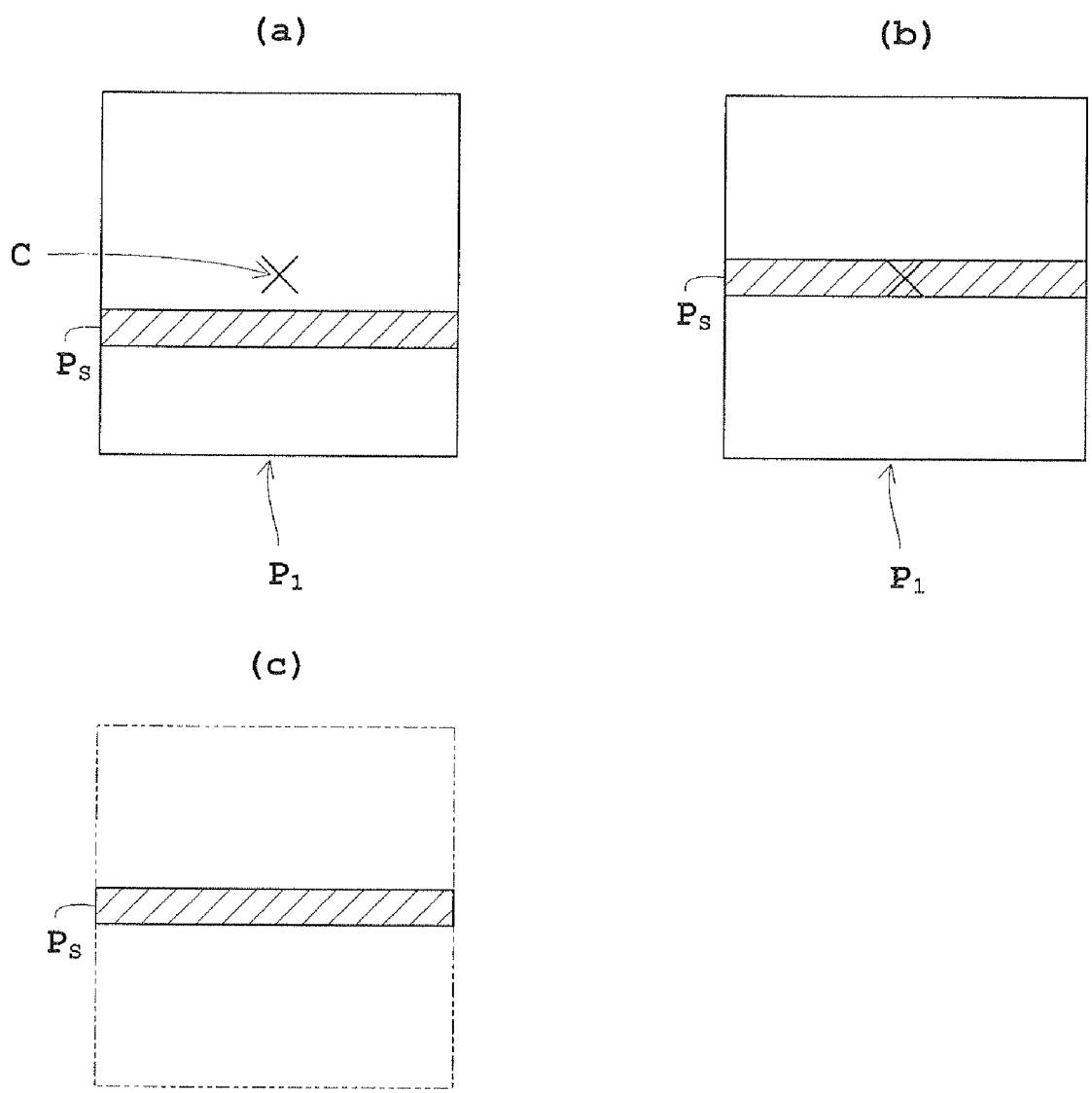
FIG. 10 is a schematic view of clipping of an effective image area.
Figure 11:
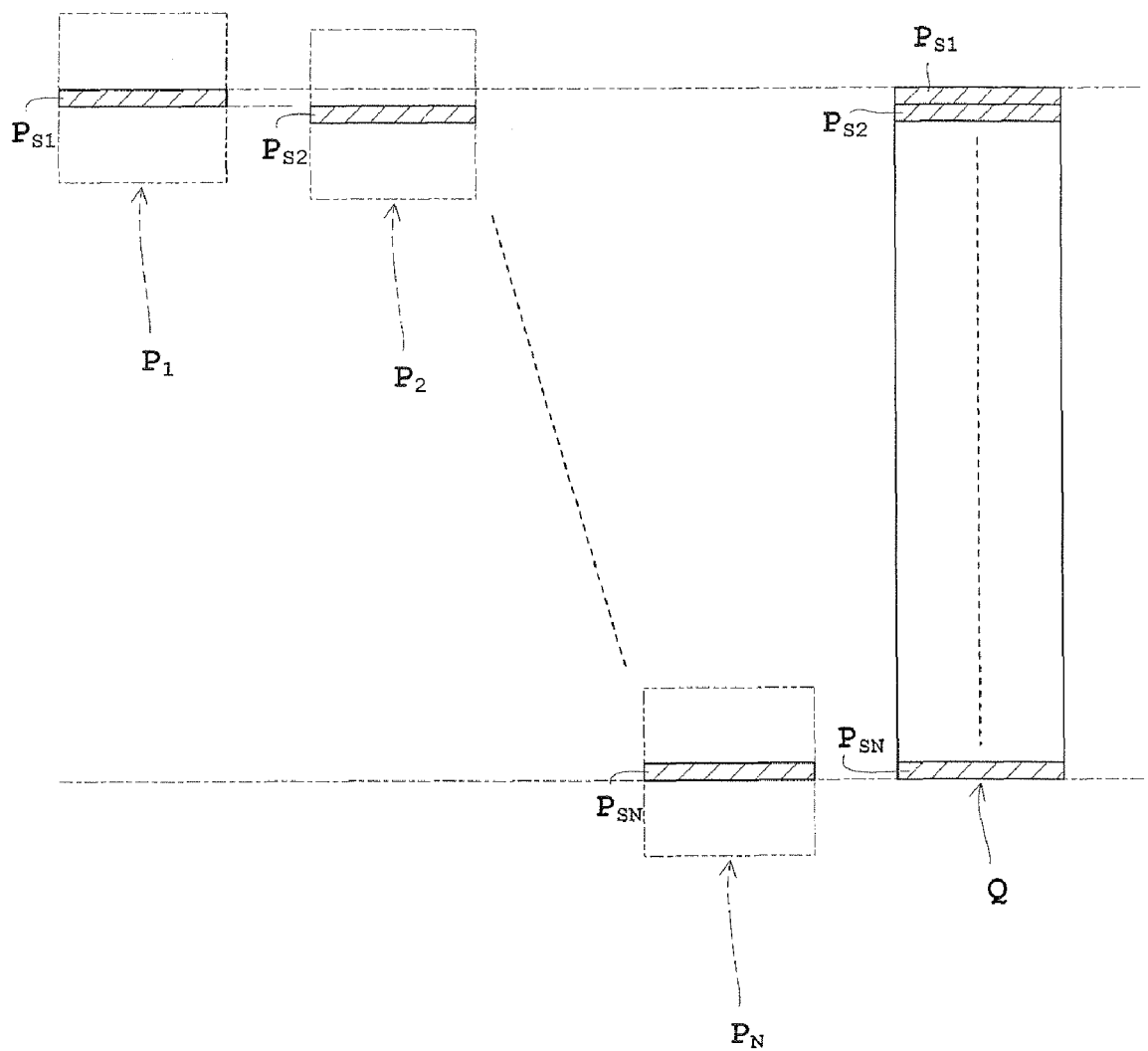
FIG. 11 is a schematic view of joining of effective image areas.

Next, specific functions of the center calculating unit 9*a*, shift calculating unit 9*b*, correcting unit 9*c*, data amount adjusting unit 9*d*, clipping unit 9*e* and joining unit 9*f* will be described hereinafter with reference to FIGS. 6-9. FIG. 6 is a schematic front view of the X-ray tube and strut at a time of standing position for illustrating occurrence of a shift due to the weight of the strut. FIG. 7 is a schematic view of X-ray images, an added image and a profile for illustrating an example of determining a shifted center of X-ray images. FIG. 8 is a schematic view of X-ray images and a peak hold image for illustrating another example of determining a shifted center of X-ray images. FIG. 9 is a schematic view showing each example about selection of a predetermined pixel area narrower than an entire pixel area of an X-ray image. FIG. 10 is a schematic view of clipping of an effective image area. FIG. 11 is a schematic view of joining of effective image areas.

As noted in the [PROBLEM TO BE SOLVED BY THE INVENTION] section, and as shown in FIG. 6, the strut 21 supporting the X-ray tube 2 sags under its own weight when in the standing position including also the inclined position. Therefore, the X-ray tube 2, which should normally be in the position of the two-dot chain lines in FIG. 6, will shift to the position of the solid lines. As a result, the center C of X-ray images normally obtained from imaging will shift to C' due to the weight of the strut 21.

So, in Embodiment 1, in the presence of such shift, X-ray images are acquired based on X-rays detected (X-ray detection signals) with the irradiation field restricted to be narrow by the collimator 22. To state the procedure of slot imaging more specifically, the collimator 22 controls the irradiation field emitted from the X-ray tube 2 to be narrower than the irradiation field projected to the FPD 3, and with the irradiation field restricted to be narrow by the collimator 22, X-ray imaging is carried out in which, while the X-ray tube 2 and FPD 3 move parallel to each other relative to the top board 1 in the same direction along the longitudinal direction of the patient M, the X-ray tube 2 emits X-rays, and the FPD 3 detects the X-rays. When a shift occurs due to the weight of the tilted strut 21, imaging is carried out in one operation, in the presence of the shift, for acquiring a plurality of X-ray images based on X-rays detected with the irradiation field restricted to be narrow by the collimator 22.

As shown in FIG. 7 (a), these plurality of X-ray images $P_1$, $P_2$, ... acquired are added on a pixel-by-pixel basis (noted "Addition" in FIG. 7 (a)). An added image $P_{add}$ obtained from the addition is as shown in FIG. 7 (b). In FIGS. 7 (a) and FIG. 7 (b), with the projection in the longitudinal direction indicated by arrows in the figures, since the plurality of X-ray images $P_1$, $P_2$, ... in FIG. 7 (a) are images picked up with the irradiation field restricted to be narrow, the areas hatched with diagonal lines extending to the upper right in the X-ray images $P_1$, $P_2$, ... have higher pixel values than the other pixel areas. Similarly, in the added image $P_{add}$ obtained from the addition, shown in FIG. 7 (b), the area hatched with diagonal lines extending to the upper right has higher pixel values than the other pixel areas.

A profile of the pixel values (X-ray detection signals) of the positions of the projection in the longitudinal direction is prepared as shown in FIG. 7 (c). The horizontal axis represents the positions of the projection in the longitudinal direction (noted "position" in FIG. 7 (c)). The vertical axis represents the pixel values (X-ray detection signals) (noted "signal" in FIG. 7 (c)). Then, the areas hatched with diagonal lines extending to the upper right (i.e. the areas having higher pixel values than the other pixel areas) shown in FIGS. 7 (a) and FIG. 7 (b) are distributed as the area hatched with diagonal lines extending to the upper right shown in FIG. 7 (c). A pixel having a maximum pixel value (noted "Max" in FIG. 7 (c)) is selected from these positions of the projection in the longitudinal direction.

Although this pixel having a maximum pixel value can be regarded as shifted center C' of the X-ray images, the distribution of the profile is not necessarily a normal distribution but may deviate from the center. In that case, each edge (noted "Edge" in FIG. 7 (c)) is detected based on a less than one threshold (noted "SH" in FIG. 7 (c)) of the selected maximum pixel value. Specifically, pixels (positions) having a pixel value of the maximum multiplied by the threshold is detected as edges. Since they are distributed to both sides of the center, two edges are detected. The center between the respective detected edges is determined the shifted center C' of the X-ray image. The threshold is about 30%, for example. The threshold corresponds to the predetermined ratio of less than one in this invention. In this way, based on the added image $P_{add}$ obtained by adding the plurality of X-ray images $P_1$, $P_2$, ..., the center calculating unit 9a (see FIG. 3) determines the shifted center C' of the X-ray images.

Apart from the added image $P_{add}$, the center calculating unit 9a (see FIG. 3) can derive the shifted center C' of the X-ray images from a peak hold image $P_{PH}$ as shown in FIG. 8. That is, an operation for selecting a maximum pixel value (noted "Max" in FIG. 8) of the same pixel (x, y) throughout the plurality of X-ray images $P_1$, $P_2$, ... is carried out with respect to other same pixels. An image composed of the pixels having the selected maximum pixel value serves as the peak hold image $P_{PH}$.

When deriving the shifted center C' of the X-ray images from the peak hold image $P_{PH}$, the shifted center C' of the X-ray images may be determined in the same way as FIG. 7 (c), using the peak hold image $P_{PH}$ instead of the added image. That is, the profile shown in FIG. 7 (c) may be prepared from the peak hold image $P_{PH}$, each edge may be detected based on the threshold, and the center between the respective detected edges may be determined the shifted center C' of the X-ray image.

When deriving the shifted center C' of the X-ray images from a plurality of X-ray images (after obtaining the added image $P_{add}$ or peak hold image $P_{PH}$), it is possible to use a plurality of X-ray images obtained by a current imaging event, and use all the pixel areas thereof. However, for enabling the center calculating unit 9a (see FIG. 3) to perform a high-speed arithmetic process, the following measure is preferred.

That is, it is preferred that a predetermined number of frames of X-ray image are selected from a plurality of X-ray images, and the center calculating unit 9a determines the shifted center C' the X-ray images based only on the selected X-ray images. Although there is no limitation as to the number of frames selected, X-ray images may be picked out every n frames, for example, to select the X-ray images picked out or X-ray images remaining after the picking. By determining the shifted center C' of the X-ray images without using all the plurality of X-ray images, the center calculating unit 9a can perform a high-speed arithmetic process.

It is also preferred that a predetermined pixel area smaller than an entire pixel area is selected from the entire pixel area of a plurality of X-ray images, and the center calculating unit 9a determines the shifted center C' the X-ray images based only on the selected pixel area. Although there is no limitation as to the pixel area selected, the pixel area, preferably, includes the vicinity of the center of the pixel area, considering that the center is to be determined. For example, a pixel area Cal to be selected (subject for operation) may be an area including a presumed area hatched with diagonal lines extending to the upper right as shown in FIG. 9 (a), or may be the presumed area hatched with diagonal lines extending to the upper right as shown in FIG. 9 (b). As shown in FIG. 9 (c), it is not necessary to include, as subject for operation, opposite end regions in the direction (transverse direction) perpendicular to the longitudinal direction. In addition, it is possible to pick out pixels, X in number, and select pixel areas picked out or pixel areas remaining after the picking. By determining the shifted center C' of the X-ray images without using the entire pixel area of the plurality of X-ray images, the center calculating unit 9a can perform a high-speed arithmetic process.

If the number of frames or pixel areas is adjusted in this way, it is possible to adjust the amount of data of X-ray images. Then, the data amount adjusting unit 9d (see FIG. 3) adjusts the amount of data used by the center calculating unit 9a, based on the amount of data of a plurality of X-ray images. For expediency of description, on an assumption that the amount of data increases in proportion to the number of pixels or the number of frames, M=K×n×X where X is the number of pixels per unit frame used by the center calculating unit 9a, n is the number of frames used by the center calculating unit 9a, K is a proportional constant, and M is an amount of data used by the center calculating unit 9a.

In this case, when there is a large amount of data of a plurality of X-ray images, the data amount adjusting unit 9d adjusts the amount of data M to be less by reducing the number of pixels X (narrowing pixel areas) or reducing the number of frames n used by the center calculating unit 9a, thereby to accelerate the arithmetic process by the center calculating unit 9a to high speed. Conversely, when there is a small amount of data of a plurality of X-ray images, the data amount adjusting unit 9d adjusts the amount of data M to be more by increasing the number of pixels X (enlarging pixel areas) or increasing the number of frames n used by the center calculating unit 9a, thereby to render the arithmetic process by the center calculating unit 9a accurate. Thus, with the data amount adjusting unit 9d adjusting the amount of data, the arithmetic process by the center calculating unit 9a can be made as desired.

After the center calculating unit 9a determines the shifted center C' of the X-ray image, the shift calculating unit 9b derives a shift of the center of the X-ray images from a positional relationship between the shifted center C' of the X-ray images and the irradiation field of the FPD 3 (the normal center C of the X-ray images in FIG. 6, i.e. the center C of the irradiation field of the FPD 3). Regarding the center of the irradiation field of the FPD 3, the address (pixel) of the center position may be determined to be the center from longitudinal and transverse (pixels) of actual images projected to the FPD 3. Assuming the determined shift (C'−C=) ΔX, the correcting unit 9c subtracts the shift ΔX from the above-noted plurality of X-ray images per se, respectively, thereby correcting the shift for the X-ray images per se.

Before the correction, the detected X-ray detection signals are read through the amplifiers 38, data bus lines 39 and analog-to-digital converter 8 (see FIG. 5). At the reading time, X-ray detection signals corresponding to all the pixel areas of the X-ray images are read. As shown in FIG. 10, P denotes an X-ray image representing the plurality of X-ray images $P_1$, $P_2$, . . . , and $P_S$ denotes an effective pixel area corresponding to the irradiation field restricted to be narrow by the collimator 22. Before the correction, the effective pixel area $P_S$ is displaced from the center C of the irradiation field as shown in FIG. 10 (a). Then, the correction by the above correcting unit 9c corrects the center of effective pixel area $P_S$ into agreement with the center C of the irradiation field as shown in FIG. 10 (b). The clipping unit 9e (see FIG. 3) clips the effective pixel area $P_S$ corrected in this way from the entire pixel area of X-ray image P as shown in FIG. 10 (c).

The joining unit 9f (see FIG. 3) joins, in the longitudinal direction, effective pixel areas $P_S$ clipped in this way for the respective X-ray images. As shown in FIG. 11, when the X-ray images are labeled $P_1, P_2, \ldots P_N$, the effective pixel area of X-ray image $P_1$ is labeled $P_{S1}$, the effective pixel area of X-ray image $P_2$ is labeled $P_{S2}$, and similarly the effective pixel area of X-ray image $P_N$ is labeled $P_{SN}$, the clipped effective pixel areas $P_{S1}$ and $P_{S2}$ are joined in the longitudinal direction. Similarly, subsequent joining is carried out in order, and an image Q is obtained from the joining operation.

According to the X-ray imaging apparatus in Embodiment 1, imaging (slot imaging) is carried out in one operation for obtaining X-ray images based on X-rays detected (X-ray detection signals) with the irradiation field restricted to be narrow by the collimator 22. Since these plurality of X-ray images are images picked up with the irradiation field restricted to be narrow, the center calculating unit 9a can determine the shifted center C' of the X-ray images as shown in FIG. 7. The shift calculating unit 9b derives shift ΔX of the center of the X-ray images from the positional relationship between the shifted center C' of the X-ray images determined and the irradiation field of the FPD 3. Since the correcting unit 9c corrects the shift for the above-noted plurality of X-ray images per se based on the shift ΔX determined, the shift can be corrected in one slot imaging operation. At a time of slot imaging, the shift can be corrected while determining a central point at a point of time when each image is acquired, or determining a central point all together after acquiring a series of images.

Embodiment 1 uses, as data based on a plurality of X-ray images, the added image $P_{add}$ obtained by adding the plurality of X-ray images $P_1, P_2, \ldots$, or the image (i.e. peak hold image) $P_{PH}$ obtained by carrying out an operation for selecting a maximum pixel value of the same pixel (x, throughout the plurality of X-ray images $P_1, P_2, \ldots$, with respect to other same pixels, and combining pixels having the selected maximum pixel value. And the center calculating unit 9a determines shifted center C' of the X-ray images based on the added image $P_{add}$ or peak hold image $P_{PH}$.

In Embodiment 1, as one example in which the center calculating unit 9a determines the shifted center C' of the X-ray images, the center calculating unit 9a, based on the plurality of X-ray images, selects a pixel having a maximum pixel value from all pixels, detects each edge based on a predetermined ratio of less than one (threshold in Embodiment 1) of the selected maximum pixel value, and determines the center between the detected edges to be the shifted center C' of the X-ray images. Of course, when the distribution of the profile shown in FIG. 7 (c) is a normal distribution, the pixel having a maximum pixel value may be regarded as the shifted center C' of the X-ray images.

In Embodiment 1, when the top board 1 is rotated and tilted about the axis of the horizontal shaft, with this tilting the X-ray tube 2 and FPD 3 tilt, and so does the strut 21 supporting the X-ray tube 2. When the strut 21 tilts with the above tilting, and a shift is caused by the weight of the strut 21 due to the tilting, the shift displaces the center of X-ray images. In such a case also, at a time of slot imaging, the shift can be corrected while determining a central point at a point of time when each image is acquired, or determining a central point all together after acquiring a series of images.

In Embodiment 1, the clipping unit 9e is provided for clipping a pixel area (i.e. an effective image area) corresponding to the irradiation field restricted to be narrow by the collimator 22, from each X-ray image corrected by the correcting unit 9c. Since the above effective image area is clipped in the state of having been corrected, this can prevent a situation where an area without valid data is clipped.

When the above clipping unit 9e is provided, Embodiment 1 includes the joining unit 9f for joining, in the longitudinal direction, the effective image areas clipped by the clipping unit 9e for the respective X-ray images. An X-ray image Q joined in the longitudinal direction (see FIG. 11) can be obtained by joining the clipped effective image areas in the longitudinal direction for the respective X-ray images.

Usually, when the above clipping unit 9e is provided, the amplifiers 38, data bus lines 39 and analog-to-digital converter 8 are provided for reading detected X-rays (X-ray detection signals) when correcting a shift while determining a central point at a point of time when each image is acquired, or determining a central point all together after acquiring a series of images. After reading X-rays (X-ray detection signals) for an entire pixel area of the X-ray images through these amplifiers 38, data bus lines 39 and analog-to-digital converter 8, the correcting unit 9c corrects a shift for X-ray images based on the read X-rays (X-ray detection signals), and the clipping unit 9e clips effective image areas restricted to be narrow from the entire pixel areas of the X-ray images corrected.

[Embodiment 2]

Figure 12:
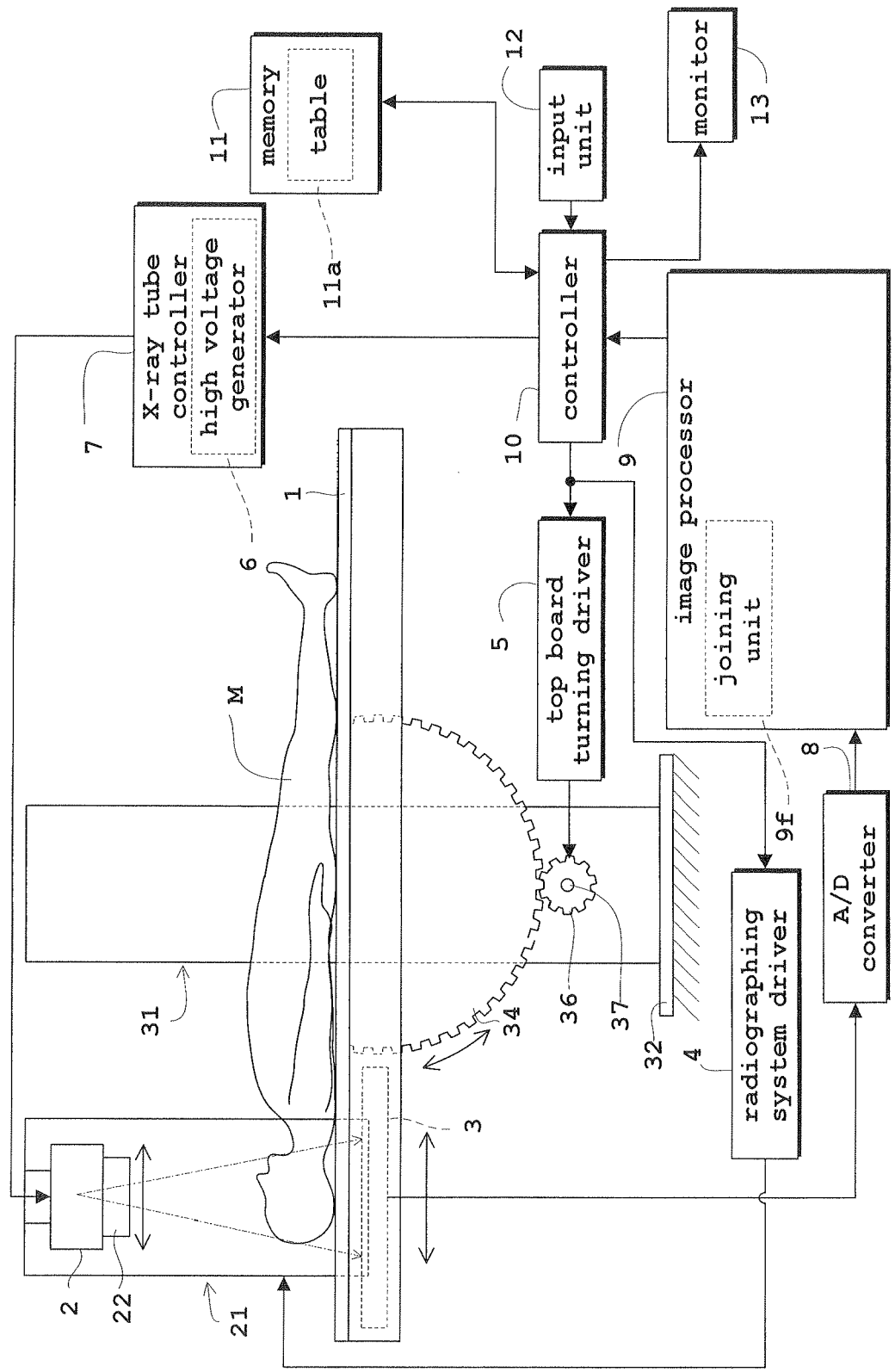
FIG. 12 is a schematic side view and block diagram of the X-ray imaging apparatus according to Embodiment 2.
Figure 13:
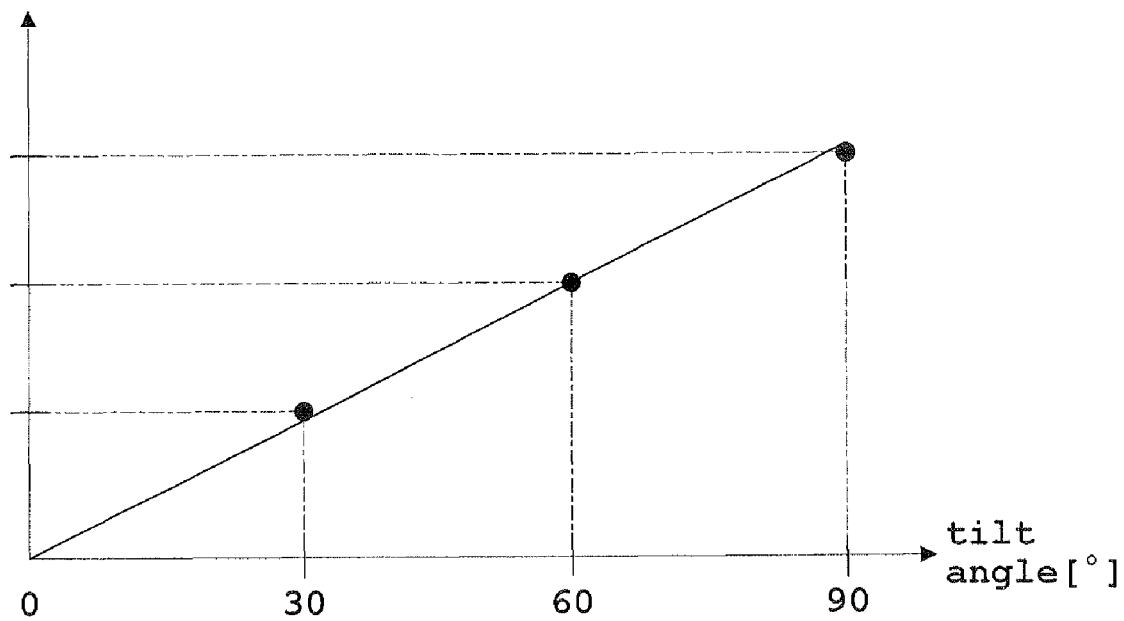
FIG. 13 is a graph showing a relationship between tilt angle relating to the tilting and shift of the center of X-ray images according to Embodiments 2 and 3.

Next, Embodiment 2 of this invention will be described hereinafter with reference to the drawings. FIG. 12 is a schematic side view and block diagram of an X-ray imaging apparatus according to Embodiment 2. FIG. 13 is a graph showing a relationship between tilt angle relating to the tilting and shift of the center of X-ray images according to Embodiment 2, including also Embodiment 3 to follow. Parts identical to those of Embodiment 1 are affixed with the same reference numbers, and are not described again.

In Embodiment 2, excepting the functions of the image processor 9, memory 11 and gate driver 35 (see FIG. 5), the X-ray imaging apparatus is the same as in Embodiment 1 in the other aspects of the construction, which will not be described.

In Embodiment 2, the memory 11 has a table 11a storing a relationship between tilt angle (turning angle) relating to the tilting and shift of the center of X-ray images (see FIG. 13). In Embodiment 2, the image processor 9 does not include the center calculating unit 9a, shift calculating 9b, correcting unit 9c, data amount adjusting unit 9d or clipping unit 9e in Embodiment 1 described hereinbefore (see FIG. 3), but includes only the joining unit 9f. Also in Embodiment 2, the joining unit 9f corresponds to the joining device in this invention.

The above table 11a stores a relationship between tilt angle (turning angle) relating to the tilting and shift of the center of X-ray images, which is as shown in FIG. 13, for example. Specifically, in advance of slot imaging, a shift is measured at each varied tilt angle. The technique of determining a shift may be such that, at a certain tilt angle, a shifted center of X-ray images is determined as in foregoing Embodiment 1, and a shift of the center of the X-ray images is determined from the positional relationship between the shifted center of the X-ray images and the irradiation field of the FPD 3.

For example, shifts may be measured when the tilt angles are 0°, 30°, 60° and 90°, respectively, and for other angles, interpolations may be made based on the shifts for the tilt angles of 0°, 30°, 60° and 90°. For example, an approximate equation expressing the relationship between tilt angle and shift may be obtained by the method of least squares from the data of shifts for the tilt angles of 0°, 30°, 60° and 90° (see the linear direct function in FIG. 13), and shifts may be determined by substituting tilt angles into the approximate equation. The table 11a stores, besides the data of shifts for the tilt angles of 0°, 30°, 60° and 90°, the data of shifts for other tilt angles interpolated using the above approximate equation, and stores the data of shifts as corresponding to varied tilt angles, respectively.

In addition to the table 11a storing the above relationship between tilt angle and shift, the memory 11 stores a program of the above approximate equation. A shift at the time of a certain tilt angle can be determined through the program executed by the central processing unit (CPU) such as of the controller 10 or image processor 9. Although FIG. 13 shows a graph of linear direct function, any graph presenting the relationship between tilt angle and shift may of course be used without being limited to the linearity.

With a shift corrected based on the relationship stored in the table 11a, an effective image area $P_S$ (see FIG. 10) is determined as a read range. Specifically, an effective image area $P_S$ as shown in FIG. 10 (a) is known as in foregoing Embodiment 1 before reading of the detected X-rays (X-ray detection signals). This effective image area $P_S$, which is before correction, is corrected as shown in FIG. 10 (b), as in foregoing Embodiment 1. Since the effective image area $P_S$ corrected, and also before being corrected, is an area corresponding to the irradiation field restricted to be narrow by the collimator 22, the longitudinal and transverse addresses (pixels) of the image to be read are known, and so are the gate bus lines 35 and data bus lines 39 (see FIG. 5) for reading.

Therefore, when the X-ray tube controller 7 sets and controls the irradiation field of the collimator 22 to be narrow, the control data is sent to the gate driver 35 (see FIG. 5) and the like. The gate driver 35 and the like convert it into addresses of the gate bus lines 35 and data bus lines 39 to be used for reading. By designating these gate bus lines 35 and data bus lines 39, a range to be read is determined in a state of a shift being corrected. It should be noted that FIG. 10 (a) and FIG. 10 (b) show images before the reading, in Embodiment 2, unlike in foregoing Embodiment 1. In Embodiment 2, the gate driver 35 corresponds to the read range calculating device in this invention.

And based on the read range determined by the gate driver 35 and the like, the detected X-rays (X-ray detection signals) corresponding to the effective image area $P_S$ are read through the amplifiers 38, data bus lines 39 and analog-to-digital converter 8 (see FIG. 5), thereby obtaining the effective image area $P_S$ with the shift corrected as shown in FIG. 10 (b). In Embodiment 2 also, the amplifiers 38, data bus lines 39 and analog-to-digital converter 8 correspond to the reading device in this invention. The joining by the joining unit 9f is the same as in foregoing Embodiment 1, and is not described here.

According to the X-ray imaging apparatus in Embodiment 2, imaging (slot imaging) is carried out for obtaining X-ray images based on X-rays detected (X-ray detection signals) with the irradiation field restricted to be narrow by the collimator 22. On the other hand, when the top board 1 is rotated and tilted about the axis of the horizontal axis, with this tilting the X-ray tube 2 and FPD 3 tilt. So, the relationship between tilt relating to inclination and shift of the center of X-ray images is stored beforehand in the table 11a of the memory 11, and in the state of a shift corrected based on the relationship stored in the table 11a, a pixel area corresponding to the irradiation field restricted by the collimator 22 (i.e. effective image area) is determined as a read range. Based on the read range, the amplifiers 38, data bus lines 39 and analog-to-digital converter 8 read detected X-rays corresponding to the effective image area, thereby correcting a shift caused by a tilt angle at a time of slot imaging.

In Embodiment 2, the joining unit 9f is provided for joining, in the longitudinal direction, the effective image areas of the X-ray images based on the X-rays read by the amplifiers 38, data bus lines 39 and analog-to-digital converter 8. An X-ray image Q joined in the longitudinal direction (see FIG. 11) can be obtained by joining the read effective image areas in the longitudinal direction for the respective X-ray images.

[Embodiment 3]

Figure 14:
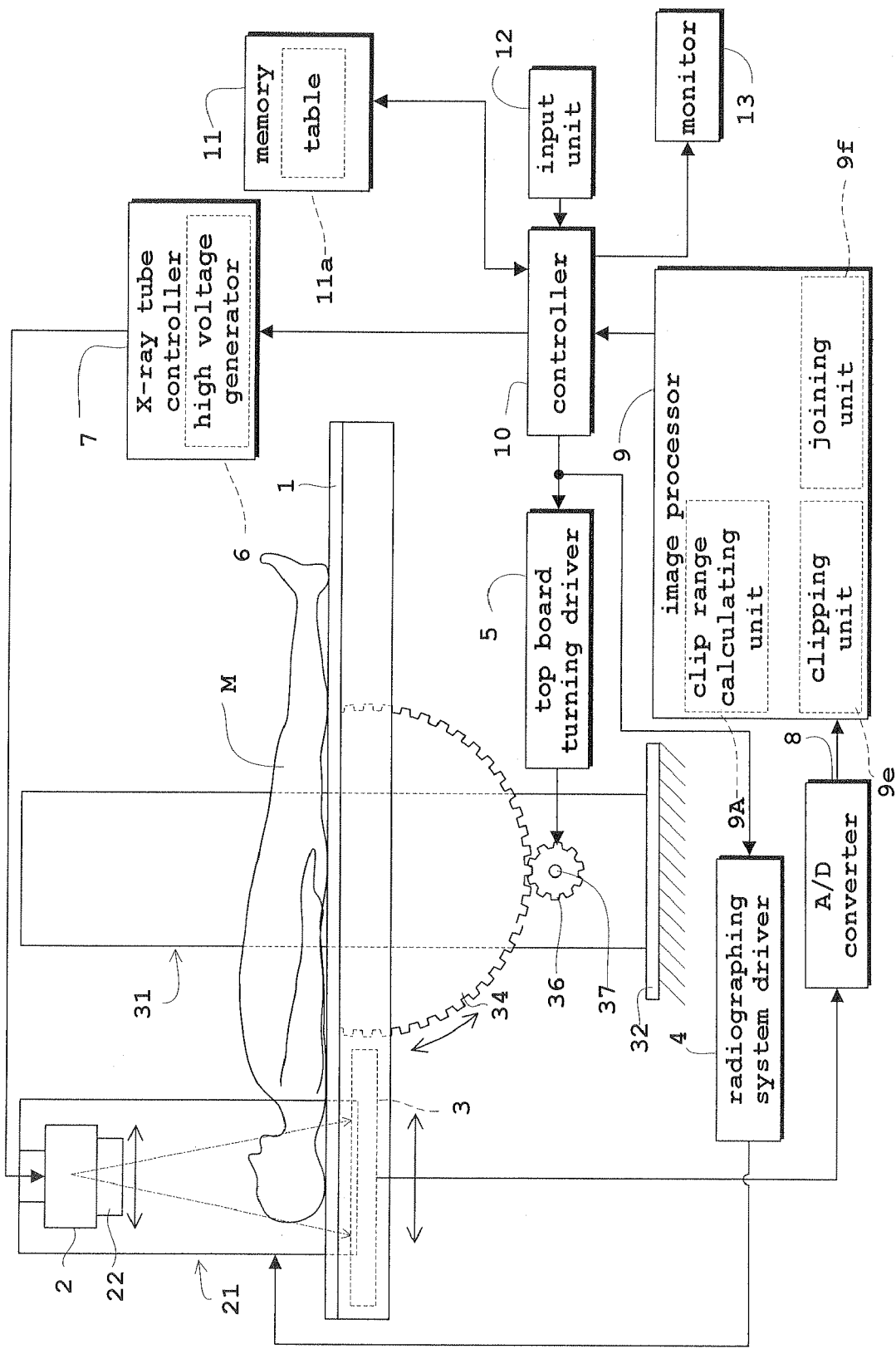
FIG. 14 is a schematic side view and block diagram of the X-ray imaging apparatus according to Embodiment 3.

Next, Embodiment 3 of this invention will be described hereinafter with reference to the drawings. FIG. 14 is a schematic side view and block diagram of an X-ray imaging apparatus according to Embodiment 3. Parts identical to those of foregoing Embodiments 1 and 2 are affixed with the same reference numbers, and are not described again.

In Embodiment 3, excepting the functions of the image processor 9 and memory 11, the X-ray imaging apparatus is the same as in Embodiment 1 in the other aspects of the construction, which will not be described.

In Embodiment 3, the memory 11 has a table 11a storing a relationship between tilt angle (turning angle) relating to the tilting and shift of the center of X-ray images (see FIG. 13). The function of this table 11a is the same as in foregoing Embodiment 2, and is not described here. In Embodiment 3, the image processor 9 does not include the center calculating unit 9a, shift calculating 9b, correcting unit 9c or data amount adjusting unit 9d in Embodiment 1 described hereinbefore (see FIG. 3), but includes the clipping unit 9e and joining unit 9f. In addition, the image processor 9 includes a clip range calculating unit 9A. Also in Embodiment 3, the clipping unit 9e corresponds to the clipping device in this invention. The joining unit 9f corresponds to the joining device in this invention. The clip range calculating unit 9A corresponds to the clip range calculating device in this invention.

Embodiment 3, as does foregoing Embodiment 1, includes the reading device having the amplifiers 38, data bus lines 39 and analog-to-digital converter 8. Unlike foregoing Embodiment 2, a read range is not determined before reading. With a shift corrected based on the relationship stored in the table 11a for the X-ray images based on the read X-rays (X-ray detection signals), an effective image area $P_S$ (see FIG. 10) is determined as a clip range. Specifically, after reading the detected X-rays (X-ray detection signals), as in foregoing Embodiment 1, the effective image area $P_S$ of FIG. 10 (a) is corrected as shown in FIG. 10 (b). It should be noted that, in this embodiment, as distinct from foregoing Embodiment 2, and as in foregoing Embodiment 1, FIG. 10 (a) and FIG. 10 (b) are images after the reading. Based on the clip range determined as shown in FIG. 10 (b), the clipping unit 9e clips the effective image area $P_S$ from the entire pixel area of X-ray image P as shown in FIG. 10 (c). The joining by the joining unit 9f is the same as in foregoing Embodiments 1 and 2, and its description is omitted.

According to the X-ray imaging apparatus in Embodiment 3, imaging (slot imaging) is carried out for obtaining X-ray images based on X-rays detected (X-ray detection signals) with the irradiation field restricted by the collimator 22. On the other hand, when the top board 1 is rotated and tilted about the axis of the horizontal axis, with this tilting the X-ray tube 2 and FPD 3 tilt. So, the relationship between tilt angle relating to the tilting and shift of the center of X-ray images is stored beforehand in the table 11a of the memory 11, and in the state of a shift corrected based on the relationship stored in the table 11a for the X-ray images based on the X-rays read by the amplifiers 38, data bus lines 39 and analog-to-digital converter 8, a pixel area corresponding to the irradiation field restricted by the collimator 22 (i.e. effective image area) is determined as a clip range. Based on the clip range, the clipping unit 9e clips the effective image area from the entire pixel area of the X-ray image, thereby correcting a shift caused by a tilt angle at a time of slot imaging.

Embodiment 3 includes the joining unit 9f for joining, in the longitudinal direction, the effective image areas clipped by the above clipping unit 9e for the respective X-ray images. An X-ray image Q joined in the longitudinal direction (see FIG. 11) can be obtained by joining the clipped effective image areas in the longitudinal direction for the respective X-ray images.

This invention is not limited to the foregoing embodiments, but may be modified as follows:

(1) In each of the foregoing embodiments, the X-ray imaging apparatus has been described as an example of radiographic apparatus. The invention may be applied to a radiographic apparatus, such as an ECT (Emission Computed Tomography) apparatus represented by a PET (Positron Emission Tomography) apparatus or a SPECT (Single Photon Emission CT) apparatus, which carries out radiation image pickup by detecting radiation other than X-rays (gamma rays in the case of the PET apparatus) and obtaining radiographic images based on the detected radiation.

(2) In each of the foregoing embodiments, the flat panel X-ray detector has been described as an example of radiation detecting device. There is no limitation as long as the device is an X-ray detecting device used generally, such as an image intensifier (I.I.). As in the case of being applied to an ECT apparatus, as in modification (1) above, there is no limitation as long as it is a radiation detecting device used generally.

(3) In each of the foregoing embodiments, the receiving device represented by the top board is constructed controllable to a horizontal position, and controllable to a standing position along the vertical direction. As long as the receiving device is constructed tiltable through rotation about the axis of a horizontal shaft, there is no need to construct it controllable completely to the horizontal position or standing position. Although each embodiment has been described taking the case of correcting a shift occurring in the standing position for example, a similar operation may be carried out in the case of inclined positions (0°<θ<90°) other than the standing position.

(4) In each of the foregoing embodiments, the radiation emitting device represented by the X-ray tube and the radiation detecting device represented by the FPD are moved parallel to each other in the same direction along the longitudinal direction of the patient M relative to the receiving device represented by the top board. As long as the radiation emitting device and radiation detecting device are moved parallel to each other in the same direction along the longitudinal direction of the patient relative to the receiving device, the radiation emitting device and radiation detecting device may be fixed, and only the receiving device may be moved parallel along the longitudinal direction of the patient. With the radiation emitting device and radiation detecting device moved parallel along the longitudinal direction of the patient, the receiving device may be moved in a counter direction, or may be moved parallel along the longitudinal direction of the patient faster or slower than a moving speed of the radiation emitting device and radiation detecting device.

(5) Foregoing Embodiment 1 has been described taking an added image or a peak hold image as an example of data based on a plurality of radiographic images (X-ray images in Embodiment 1), but this is not limitative. For example, a profile may be prepared for each of a plurality of radiographic images, and a shifted center of the radiographic images may be determined based on a profile obtained by adding the profiles the respective radiographic images.

Figure 15:
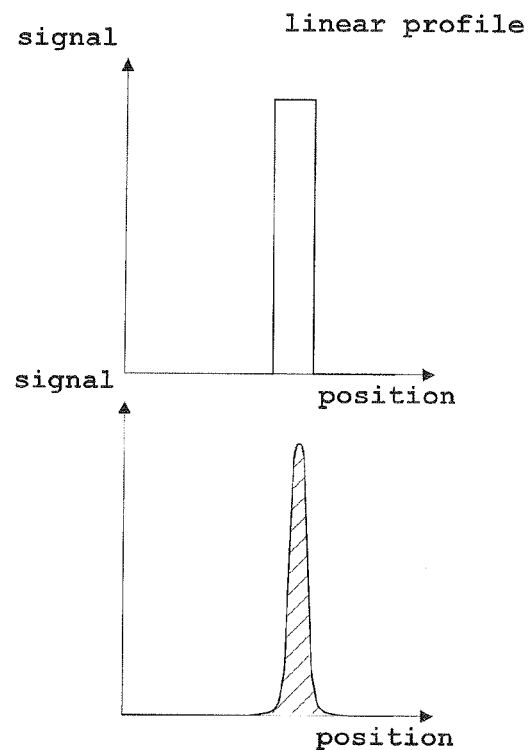
FIG. 15 is a schematic view of a linear profile and an actually imaged profile.
Figure 16:
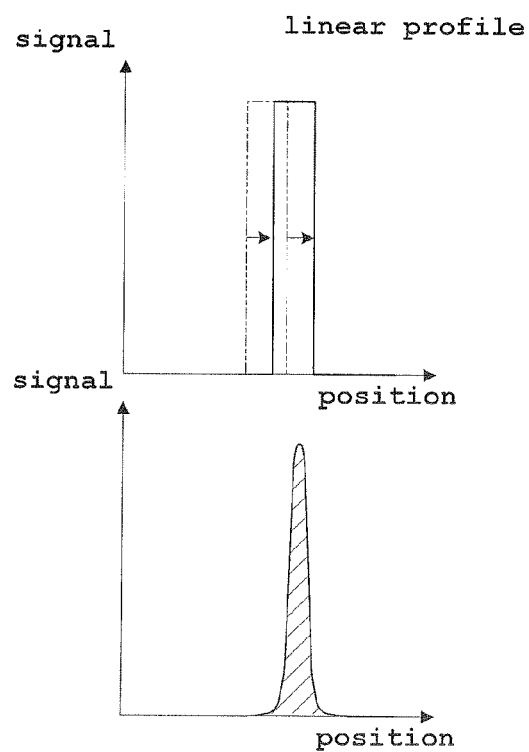
FIG. 16 is a schematic view of a linear profile and an actually imaged profile.

(6) In foregoing Embodiment 1, as one example of determining a shifted center of radiographic images (X-ray images in Embodiment 1), a pixel having a maximum pixel value is selected from all pixels, based on the plurality of radiographic images, each edge is detected based on a predetermined ratio of less than one (threshold in Embodiment 1) of the selected maximum pixel value, and the center between the detected edges is determined to be the shifted center of the radiographic images. This is not limitative. As shown in FIG. 15, for example, a profile for linear model may be prepared, with the linear profile and the profile prepared as shown in FIG. 7 (c), the profiles may be integrated for each position of longitudinal projection, and a pixel having a maximum pixel value among the values obtained by integration may be regarded as the shifted center of the radiographic images. As shown in FIG. 16, the linear profile may be moved in the longitudinal direction, with a linear profile obtained by each movement and the profile prepared as shown in FIG. 7 (c), the profiles may be integrated for each position of longitudinal projection, and a pixel having a maximum pixel value among the values obtained by integration may be regarded as the shifted center of the radiographic images.

(7) Foregoing Embodiment 1 includes the correction device (correcting unit in Embodiment 1). However, the correction device is not absolutely necessary, where the shifted center of radiographic images (X-ray images in Embodiment 1) determined by the shift calculating device (shift calculating unit in Embodiment 1) is fed into an external apparatus, and a correction device in the external apparatus corrects the shift determined by the shift calculating device.

(8) In each of the foregoing embodiments, the invention is applied to the apparatus which tilts the receiving device represented by the top board. The invention may be applied to an apparatus for carrying out ordinary slot imaging without tilting the receiving device, where the receiving device (top board in the embodiments) is not tilted or turned, but the center of radiographic images (X-ray images) shifts mechanically.

The invention claimed is:

1. A radiographic apparatus having a receiving device for receiving a patient thereon, a radiation emitting device, with an irradiation field control device for emitting radiation toward the patient, a radiation detecting device for detecting radiation transmitted through the patient to carry out radiographic imaging by obtainig radiographic images based on the detected radiation, the irradiation field control device controlling and restricting an irradiation field emitted from the radiation emitting device to be narrower than an irradiation field projected to the radiation detecting device, the radiographic imaging being carried out with the radiation emitting device emitting radiation and the radiation detecting device detecting the radiation while, with the irradiation field restricted to be narrow by the irradiation field control device, the radiation emitting device and the radiation detecting device move parallel to each other in the same direction along a longitudinal direction of the patient relative to the receiving device, the apparatus comprising a center calculating device for determining a shifted center of radiographic image detected in a state of the irradiation field restricted to be narrow by the irradiation field control device, and a shift calculating device for determining a shift of the center of the radiographic image from a positional relationship between the center of the radiographic images and the irradiation field of the radiation detecting device.

2. The radiographic apparatus according to claim 1, wherein the center calculating device is arranged to select a predetermined number of radiographic images from the plurality of radiographic images, and determine the shifted center of the radiographic images based only on the selected radiographic images.

3. The radiographic apparatus according to claim 1, wherein the center calculating device is arranged to select a predetermined pixel area narrower than an entire pixel area from the entire pixel area of the plurality of radiographic images, and determine the shifted center of the radiographic images based only on the selected pixel area.

4. The radiographic apparatus according to claim 1, comprising a data amount adjusting device for adjusting an amount of data used by the center calculating device based on an amount of data of the plurality of radiographic images.

5. The radiographic apparatus according to claim 1, wherein the center calculating device is arranged to determine the shifted center of the radiographic images based on an added image obtained by adding the plurality of radiographic images.

6. The radiographic apparatus according to claim 1, wherein the center calculating device is arranged to carry out an operation for selecting a maximum pixel value of the same pixel throughout the plurality of radiographic images with respect to other same pixels, and determine the shifted center of the radiographic images based on an image formed of pixels having the selected maximum pixel value.

7. The radiographic apparatus according to claim 1, wherein the center calculating device is arranged, based on the plurality of radiographic images, to select a pixel having a maximum pixel value from all pixels, detect each edge based on a predetermined ratio of less than one of the selected maximum pixel value, and determine a center between the detected edges to be the shifted center of the radiographic images.

8. The radiographic apparatus according to claim 1, wherein the center calculating device is arranged, based on the plurality of radiographic images, to select a pixel having a maximum pixel value from all pixels, and determine that pixel to be the shifted center of the radiographic images.

9. The radiographic apparatus according to claim 1, wherein the radiation emitting device and the radiation detecting device are constructed, when the receiving device is rotated and tilted about an axis of a horizontal shaft, to be tiltable with that tilting, the apparatus comprising a support device tiltable with that tilting and supporting the radiation emitting device.

10. The radiographic apparatus according to claim 9, wherein the receiving device is controllable to a horizontal position.

11. The radiographic apparatus according to claim 9, wherein the receiving device is controllable to a standing position extending along a vertical direction.

12. The radiographic apparatus according to claim 1, comprising a correcting device for correcting the shift determined by the shift calculating device, for the plurality of radiographic images per se.

13. The radiographic apparatus according to claim 12, comprising a clipping device for clipping a pixel area corresponding to the irradiation field restricted to be narrow by the irradiation filed control device, from each of the radiographic images corrected by the correcting device.

14. The radiographic apparatus according to claim 13, comprising a joining device for joining, in the longitudinal direction, the pixel area clipped by the clipping device and corresponding to the irradiation field restricted to be narrow, for the respective radiographic images.

15. The radiographic apparatus according to claim 13, comprising a reading device for reading the detecting radiation, the correcting device correcting the shift, after the reading device reads radiation corresponding to an entire pixel area of the radiographic images, for a radiographic image based on the radiation read, and the clipping device clipping a pixel area corresponding to the irradiation field restricted to be narrow from the entire pixel area of the radiographic image corrected.

16. A radiographic apparatus having a receiving device for receiving a patient thereon, a radiation emitting device for emitting radiation toward the patient, a radiation detecting device for detecting radiation transmitted through the patient, and an irradiation field control device provided for the radiation emitting device for controlling and restricting an irradiation field emitted from the radiation emitting device to be narrower than an irradiation field projected to the radiation detecting device, to carry out radiographic imaging by obtaining radiographic images based on the detected radiation, the radiographic imaging being carried out with the radiation emitting device emitting radiation and the radiation detecting device detecting the radiation while, with the irradiation field restricted to be narrow by the irradiation field control device, the radiation emitting device and the radiation detecting device move parallel to each other in the same direction along a longitudinal direction of the patient relative to the receiving device, the radiation emitting device and the radiation detecting device being constructed, when the receiving device is rotated and tilted about an axis of a horizontal shaft, to be tiltable with that tilting, the apparatus comprising a storage device for storing a relationship between tilt angle relating to the tilting and shift of the center of the radiographic images, a read range calculating device for determining, as a read range, a pixel area corresponding to the irradiation field restricted to be narrow by the irradiation field control device, in a state of the shift corrected based on the relationship stored in the storage device, and a reading device for reading the detected radiation corresponding to the pixel area based on the read range.

17. The radiographic apparatus according to claim 16, comprising a joining device for joining, in the longitudinal direction, a pixel area of a radiographic image based on the radiation read by the reading device, for the respective radiographic images.

18. A radiographic apparatus having a receiving device for receiving a patient thereon, a radiation emitting device for emitting radiation toward the patient, a radiation detecting device for detecting radiation transmitted through the patient, and an irradiation field control device provided for the radiation emitting device for controlling and restricting an irradiation field emitted from the radiation emitting device to be narrower than an irradiation field projected to the radiation detecting device, to carry out radiographic imaging by obtaining radiographic images based on the detected radiation, the radiographic imaging being carried out with the radiation emitting device emitting radiation and the radiation detecting device detecting the radiation while, with the irradiation field restricted to be narrow by the irradiation field control device, the radiation emitting device and the radiation detecting device move parallel to each other in the same direction along a longitudinal direction of the patient relative to the receiving device, the radiation emitting device and the radiation detecting device being constructed, when the receiving device is rotated and tilted about an axis of a horizontal shaft, to be tiltable with that tilting, the apparatus comprising a storage device for storing a relationship between tilt angle relating to the tilting and shift of the center of the radiographic images, a reading device for reading the detected radiation, a clip range calculating device for determining, as a clip range, a pixel area corresponding to the irradiation field restricted to be narrow by the irradiation field control device, for a radiographic image based on the radiation read, in a state of the shift corrected based on the relationship stored in the storage device, and a clipping device for clipping the pixel area from an entire pixel area of the radiographic image based on the clip range.

19. The radiographic apparatus according to claim 18, comprising a joining device for joining, in the longitudinal direction, the pixel area clipped by the clipping device, for the respective radiographic images.

* * * * *